United States Patent [19]

Rossmann et al.

[11] Patent Number: 5,206,175
[45] Date of Patent: Apr. 27, 1993

[54] METHOD FOR THE DETECTION OF BIS(2-CHLOROETHYL) SULFIDE OR BIS (2-CHLOROETHYL) IMINE

[75] Inventors: Klaus Rossmann, Rumisberg, Switzerland; Wolfgang Diehl, Frankfurt, Fed. Rep. of Germany; Wolfram Krieger, Hamburg, Fed. Rep. of Germany; Jörg Boscher, Preetz, Fed. Rep. of Germany

[73] Assignee: Battelle-Institut e.V., Frankfurt, Fed. Rep. of Germany

[21] Appl. No.: 810,361

[22] Filed: Dec. 1, 1984

Related U.S. Application Data

[63] Continuation of Ser. No. 432,418, Nov. 3, 1989, filed as PCT/EP84/00383, Dec. 1, 1984, abandoned, which is a continuation of Ser. No. 298,286, Jan. 9, 1989, abandoned, which is a continuation of Ser. No. 764,257, Aug. 8, 1985, abandoned.

[30] Foreign Application Priority Data

Dec. 10, 1983 [DE] Fed. Rep. of Germany ....... 3344700

[51] Int. Cl.⁵ .................... G01N 21/64; G01N 31/22
[52] U.S. Cl. .................................. 436/106; 436/104; 436/120; 436/172
[58] Field of Search ............... 436/104, 106, 120, 162, 436/172

[56] References Cited

U.S. PATENT DOCUMENTS 3,960,759  6/1976  Mallis .................................. 436/104
4,565,787  1/1986  Bossle et al. ......................... 436/120

OTHER PUBLICATIONS

CA-99:189045b (Appler et al).
CA-96:194568s (Fritsche et al).
CA-86:154765r-Wirth P. et al.
CA-96:199415t-Kramer et al.

*Primary Examiner*—Jill A. Johnston
*Attorney, Agent, or Firm*—Spencer, Frank & Schneider

[57] ABSTRACT

The process of detecting the presence on a surface of at least one of bis(2-chloroethyl)sulfide and bis(2-chloroethyl)imine, including (a) providing a solution comprising at least one dyestuff selected from the group consisting of brilliant blue R, guinea green B, neutral red, and lissamine green B, which at least one dyestuff is capable of fluorescing and is capable, when applied as a solution, of forming an adduct with at least one of bis(2-chloroethyl)sulfide and bis(2-chloroethyl)imine when present on a surface, which at least one adduct, is capable of fluorescing in a spectral range which is different from that of the corresponding at least one dyestuff; (b) applying the solution to the surface; (c) irradiating the surface onto which the solution has been applied with light having a wavelength effective to excite the at least one dyestuff and, when present, the at least one adduct, and induce light emission by fluorescence therefrom; (d) measuring the wavelength of the light emitted from the surface; and (e) determining the presence of the at least one adduct on the surface from the presence of a measured difference in the wavelength of the light emitted by the at least one adduct and the at least one dyestuff.

14 Claims, No Drawings

METHOD FOR THE DETECTION OF BIS(2-CHLOROETHYL) SULFIDE OR BIS (2-CHLOROETHYL) IMINE

This application is a continuation of application Ser. No. 07/432,418, filed Nov. 3, 1989 and now abandoned, which is a continuation of application Ser. No. 07/298,286 filed Jan. 9, 1989 and now abandoned, which is a continuation of application Ser. No. 06/764,257 filed Aug. 8, 1985 and now abandoned.

BACKGROUND OF THE INVENTION

1. Field of the Invention

The invention relates to a method for the detection of bis(2-chloroethyl)sulfide or bis(2-chloroethyl)imine, according to which a chemical reagent is applied to the surface on which the substance to be detected is assumed to be present and the radiation thus generated is optically determined.

2. Background of the Art

Bis(2-chloroethyl)sulfide or bis(2-chloroethyl)imine is the warfare agent LOST and is usually detected on surfaces using indicators contained in paper or powder. LOST is also detected by gas chromatography after extraction from the surface. Moreover, color reactions are known which take place in aqueous or organic solutions. These reactions are carried out in test tubes.

The German Pat. No. 29 47 459 described a device for in-situ detection of precipitates of specific known agents consisting of phosphoric esters. Upon addition of indole, these compounds exhibit a chemical luminescence which can be detected without contact by means of an optical detector. However, this reaction is not applicable to the chemical warfare agent LOST.

SUMMARY OF THE INVENTION

The object of this invention is, therefore, to provide a method for the detection of LOST which can be easily realized.

This object can be achieved according to the invention with a method comprising using a dyestuff being capable of fluorescing and forming an adduct with bis(2-chloroethyl)sulfide or bis(2-chloroethyl)imine, said adduct being capable of fluorescing in a spectral range different from that of said dyestuff. Preferably, a triphenyl methane dyestuff, especially neutral red, guinea green B, lissamine green B or brilliant blue R, is sued as dyestuff. These dyestuffs are applied from aqueous/organic or organic solutions onto the surface on which the warfare agent is assumed to be present. The amount of dyestuff in the solution is between 0.001 and 0.5 weight percent, preferably between 0.01 and 0.1 weight percent.

DESCRIPTION OF THE PREFERRED EMBODIMENTS

According to the invention, dyestuffs having a reactive center are used which affect or decompose LOST nucleophilically or electrophilically, or LOST is fixed by adsorption under conformational change, or LOST is incorporated in an inclusion compound. Thereby, the characteristic fluorescence of the dyestuff is changed.

The wavelength of the excitation is preferably between 300 and 400 nm. The wavelength of the emission is preferably between 380 and 500 nm. Mixtures of water and alcohol, water and acetone or water and dimethyl formamide, or also alcohol, acetone or hexane without addition of water are preferably used as solvents for the dyestuff. Especially triphenyl methane dyestuffs are used as chemical reagents.

The invention is explained in more detail in the following examples.

EXAMPLE 1

Neutral red is dissolved in ethanol in an amount of $10^{-3}$ weight percent. Using 5 $\mu$l sulfide-LOST, an adduct is formed which, upon excitation with light of the wavelength of 330 nm exhibits fluorescence of a relative intensity of 1500 at 392 nm.

EXAMPLE 2

The method of example 1 is repeated, but in this example guinea green B is used as dyestuff. The adduct shows fluorescence of a relative intensity of 11700 at 394 nm upon excitation with light of the wavelength of 320 nm.

EXAMPLE 3

Lissamine green B is dissolved in an amount of $10^{-3}$ weight percent in a mixture of 70 percent water and 30 percent ethanol. Using 5 $\mu$l LOST an adduct is formed which, upon excitation with light of the wavelength of 340 nm, shows fluorescence of a relative intensity of 810 at 470 nm.

EXAMPLE 4

Brilliant blue R is dissolved in an amount of $2 \times 10^{-2}$ weight percent in a mixture of 70 percent water and 30 percent ethanol. The adduct obtained, upon excitation with light of the wavelength of 370 nm, shows a fluorescence of a relative intensity of 28100 at 455 nm.

What is claimed is:

1. A process of detecting the presence on a surface of at least one of bis(2-chloroethyl)sulfide or bis(2-chloroethyl)imine, comprising:
   a. providing a solution comprising at least one dyestuff selected from the group consisting of brilliant blue R, guinea green B, neutral red, and lissamine green B, which at least one dyestuff is capable of fluorescing and is capable, when applied as a solution, of forming an adduct with at least one of bis(2-chloroethyl)sulfide or bis(2-chloroethyl)imine when present on a surface, which at least one adduct is capable of fluorescing in a spectral range which is different from that of the corresponding at least one dyestuff;
   b. applying the solution to the surface;
   c. inducing fluorescence of the applied solution by irradiating the surface onto which the solution has been applied with light having a wavelength effective to excite the at least one dyestuff and, when present, the at least one adduct, and induce light emission by fluorescence therefrom;
   d. measuring the wavelength of the light emitted from the surface; and
   e. determining the presence of the at least one adduct on the surface from the presence of a measured difference in the wavelength of the light emitted by the at least one adduct and the at least one dyestuff.

2. The process according to claim 1, wherein the solution contains from 0.001 to 0.5 weight percent of the at least one dyestuff dissolved in a solvent.

3. The precess according to claim 2, wherein the solvent is one of an organic solvent and a water-organic solvent mixture.

4. The process according to claim 3, wherein the organic solvent is selected from the group consisting of alcohol, acetone, dimethyl formamide, and, when the solvent is not a water-organic solvent mixture, hexane.

5. The process according to claim 1, wherein the solution contains form 0.01 to 0.1 weight percent of the at least one dyestuff.

6. The process according to claim 5, wherein the solvent is one of an organic solvent and a water-organic solvent mixture.

7. The process according to claim 6, wherein the organic solvent is selected from the group consisting of alcohol, acetone, dimethyl formamide, and, when the solvent is not a water-organic solvent mixture, hexane.

8. The process according to claim 1, wherein the light emitted by the at least one adduct, when present, has a relative intensity at a characteristic wavelength thereof which is at least about 810.

9. The process according to claim 8, wherein the relative intensity ranges between about 810 and about 28,100.

10. The process according to claim 1, wherein the at least one dyestuff is neutral red.

11. The process according to claim 1, wherein the at least one dyestuff is selected from the group consisting of brilliant blue R, guinea green B, and lissamine green B.

12. The process according to claim 11, wherein the at least one dyestuff is brilliant blue R.

13. The process according to claim 11, wherein the at least one dyestuff is guinea green B.

14. The process according to claim 11, wherein the at least one dyestuff is lissamine green B.

* * * * *

UNITED STATES PATENT AND TRADEMARK OFFICE
CERTIFICATE OF CORRECTION

PATENT NO. : 5,206,175
DATED : April 27, 1993
INVENTOR(S) : Wolfram KRIEGER et al.

It is certified that error appears in the above-indentified patent and that said Letters Patent is hereby corrected as shown below:

On the Title page, items [22] and [56] should read as follows:

[22] Filed: December 18, 1991 -- ,

[56]  References Cited

OTHER PUBLICATIONS

CA-99:189045b (Appler et al.)

CA-96:194568s (Fritsche et al.)

CA-86:154765r (Wirth P. et al.)

CA-96:199415t (Kramer et al.) -- .

Signed and Sealed this

Twenty-fifth Day of January, 1994

Attest:

BRUCE LEHMAN

*Attesting Officer*  *Commissioner of Patents and Trademarks*